United States Patent [19]

Lukey et al.

[11] Patent Number: 5,066,629

[45] Date of Patent: Nov. 19, 1991

[54] OXIDATIVE COUPLING CATALYST FOR METHANE

[75] Inventors: Christopher A. Lukey, Queensland; Ashit M. Maitra, Hillsdale; Ralph J. Tyler, Elanora Heights, all of Australia

[73] Assignees: The Broken Hill Proprietary Company Limited, Melbourne; Commonwealth Scientific and Industrial Research Organization, Campbell, both of Australia

[21] Appl. No.: 545,958

[22] Filed: Jul. 2, 1990

[30] Foreign Application Priority Data

Jun. 30, 1989 [AU] Australia ............................... PJ5021
Aug. 16, 1989 [AU] Australia ............................... PJ5806

[51] Int. Cl.$^5$ ..................... B01J 21/16; B01J 23/02
[52] U.S. Cl. ............................................ 502/84
[58] Field of Search ....................... 502/84; 585/943

[56] References Cited

U.S. PATENT DOCUMENTS

| | | | |
|---|---|---|---|
| 1,945,960 | 2/1934 | Winker et al. | 585/943 |
| 4,450,310 | 5/1984 | Fox et al. | 585/943 |
| 4,658,077 | 4/1987 | Kolts et al. | 585/943 |
| 4,704,487 | 11/1987 | Devries et al. | 585/943 |
| 4,985,385 | 1/1991 | Williams et al. | 502/84 |
| 4,996,382 | 2/1991 | Matsuura et al. | 585/943 |

FOREIGN PATENT DOCUMENTS 210836  2/1968  U.S.S.R. ............................... 502/84

*Primary Examiner*—Carl F. Dees
*Attorney, Agent, or Firm*—Armstrong, Nikaido, Marmelstein, Kubovcik & Murray

[57] ABSTRACT

An improved catalyst for the oxidative coupling of methane containing a Group IIA element capable, under the reaction conditions, of existing at least partly in its oxide or carbonate form and a clay or a synthetic analogue of a clay. The catalyst preferably comprises an intimate mixture of strontium carbonate and bentonite, in a weight ratio of 80:20. The catalyst advantageously also contains a Group IA oxide or carbonate such as sodium carbonate.

18 Claims, 2 Drawing Sheets

5,066,629

OXIDATIVE COUPLING CATALYST FOR METHANE

FIELD OF THE INVENTION

The present invention relates to a catalyst for the oxidative coupling of a methane containing gas, such as natural gas, to higher hydrocarbons. The catalyst according to this invention will preferably convert methane to higher alkanes. These higher alkanes may in turn be converted to alkenes, principally ethylene and propylene which are major feedstocks for the petrochemical industry and are also suitable as building blocks for the subsequent production of specification grade gasoline and diesel fuel.

BACKGROUND ART

The composition of raw natural gas varies but commonly contains 75 to 85% methane together with 5 to 10% of ethane and smaller amounts of higher hydrocarbons. Ethane and higher hydrocarbons can be effectively utilised for olefin production using current technology. However, there is no significant amount of ethylene produced commercially from methane at the present time. This is due to the high stability of the methane molecule compared to other alkanes making conversion of methane to ethylene extremely difficult.

Processes involving pyrolytic dehydrogenation of methane have been proposed. However severe reaction conditions, particularly temperature, are required. In addition the process is endothermic. The severity can be reduced by the use of catalysts, but methane conversion and selectivities are still low.

An alternative approach is to react methane with oxygen in the presence of a contacting material or catalyst to produce higher hydrocarbons.

The process is generally known as "oxidative coupling". The reaction pathway has been shown to involve the oxidative extraction of a hydrogen atom from a molecule of methane by the catalyst to form a methyl ($CH_3$) radical followed by a coupling of two $CH_3$ radicals to form the primary product ethane. The desired product ethylene arises from further reactions of ethane which may or may not involve surface reactions. Other higher hydrocarbons such as propane, propylene, butylene etc. are formed in smaller amounts. Undesired products such as carbon monoxide and carbon dioxide are also formed together with water and hydrogen. The source of the carbon oxides is still uncertain but they are thought to arise initially in parallel with ethane formation and also by secondary reactions of the product hydrocarbons with oxygen either on the catalyst surface or in the gas phase.

The contribution of the catalyst to the product spectrum is uncertain and unpredictable. Furthermore, as the mechanism by which the activation of the methane molecule by the catalyst surface is largely unknown, there is at present no known method for predicting catalyst performance.

European Patent Application No. 86103623.4, Publication No. 0196541 in the name of Phillips Petroleum Company discloses oxidative coupling catalysts comprising magnesium oxide and a compound of lithium. It is also known that compounds of other Group IIA elements do have some catalytic effect on the oxidative coupling of methane. However as described in the abovementioned European Patent Application magnesium oxide is not as effective as a catalyst consisting of a mixture of magnesium oxide and a compound of lithium.

DISCLOSURE OF THE INVENTION

It has now been discovered that the effectiveness of catalysts comprising certain Group IIA or Group IIA and IA compounds is enhanced by the presence of a clay.

The present invention therefore consists in a catalyst for the oxidative coupling of methane, comprising a compound of a Group IIA element that is capable, under reaction conditions, of existing at least partly in its oxide or carbonate forms, intimately mixed with a clay capable of enhancing the catalyst performance.

In a further aspect the present invention consists in a method for the oxidative coupling of methane, comprising heating methane to a temperature of at least 700° C. in the presence of a catalyst according to the present invention.

The Group IIA compound is preferably strontium carbonate however other Group IIA oxides and carbonates, such as those of magnesium, calcium and barium, may be used with advantage. The catalyst may optionally contain a compound capable of promoting the catalyst, such as a compound of a Group IA element that is capable, under reaction conditions, of existing at least partly in its oxide or carbonate form. Lithium, sodium and potassium carbonates are preferred Group IA compounds.

It has been found that the oxidative conversion performance of a catalyst based on Group IIA elements (with or without other components added as promoters) is enhanced when the Group IIA components of the catalyst are present mainly in the oxide rather than the carbonate form under reaction conditions.

The catalysts of the present invention are highly basic and tend to form carbonates under operating conditions by combining with carbon dioxide produced during the oxidative conversion reaction. The active sites responsible for the catalytic action are thought to involve some form of oxide species and in order to maintain these species under reaction conditions, it is necessary to destabilise the carbonate form. It appears that the clay may perform some role in this destabilisation of the carbonate and the formation of catalytically active species. While the present inventors have shown that a number of clays of widely varying types show the ability to improve the activity of Group IIA oxidative coupling catalysts it is expected that there will be some clays that do not have catalyst enhancing performance. Appropriate clays may be selected using the disclosure of this specification or alternatively simple testing using the techniques described herein will enable the catalyst enhancing properties of other clays to be readily determined. As used herein the term "clay" includes naturally occurring clays as well as synthetic analogues of such natural clays.

Clays as they occur in nature are composed of extremely fine crystals or particles, often colloidal in size, of clay minerals with or without rock or other mineral particles. The clay minerals, mostly phyllosilicates with sheet or layer-like structures, are hydrous silicates of Al, Mg, Fe and other less abundant elements.

Because clays usually contain more than one mineral and the various clay minerals differ in chemical and physical properties, the term clay may signify different things to different technologists. Clay deposits often contain non-claylike minerals as impurities and these impurities may actually be essential in determining unique and especially desired properties. A broad definition includes the following properties of clays (see Kirk-Othmer Encylopaedia of Chemical Technology, 3rd Edition (1979) Wiley & Sons).

1) A predominant content of clay minerals, ranging from kaolins, which are relatively uniform in chemical composition, to smectites, which vary widely in their base exchange properties and lattice expansion and includes the illite group, chlorite minerals and vermiculite.

2) The possible content of hydrated alumina, iron or silica.

3) The extreme fineness of individual clay particles and thixotropic properties.

4) The possible content of quartz, sand, silt and many other rock and mineral particles.

Clay minerals are divided into crystalline and paracrystalline groups and an amorphous group. Some of the crystalline and paracrystalline groups and the species within the groups are shown in the table below.

| Classification of some crystalline and paracrystalline clay minerals | |
|---|---|
| Group | Species |
| Kaolins and serpentines | Kaolinite |
| | Crysotile |
| | Halloysite |
| | Dickite |
| Smectites (montmorillonites) | Montmorillonite |
| | Nontronite |
| | Saponite |
| | Sauconite |
| | Beidellite |
| | Bentonite |
| Illites or micas | |
| Glauconite | |
| Chlorites and vermiculites | |
| Attapulgite | |

Although the clays of the different groups can be similar in chemical composition they show quite different mineralogical, physical, thermal and technological properties. Chemical analysis alone has only limited value in identification whereas the mineral composition which reveals the arrangement of the constituent element is most important.

As noted previously catalyst performance varies with the type of clay used in the preparation and, as will be shown in the examples, with the treatment of the catalyst. It is believed most clays are capable of enhancing the performance of oxidative coupling catalysts, however their mode of activation may well depend on features such as mineralogical structure, nature of the layer type, degree of cation penetration between the layers and also procedures used in preparation and calcination. From a study of a variety of clays it was observed that the best performance was obtained on adding clays of the smectite group notably bentonite. As a detailed discussion of the composition and structure of clays in general is available in the literature (see for example Kirk-Othmer Encyclopaedia of Chemical Technology, 3rd Edition (1979) Wiley & Sons), comments will be limited to noting the features of the smectite group.

Smectites are 2:1 clay minerals consisting of a lattice with 2 layers of tetrahedrally coordinated Si (with O) on either side of an octahedrally coordinated Al (with O and OH) layer. This lattice is expandable between the Si layers so that when soaked in water it may swell extensively (e.g. bentonite). Residual charge can arise on the clay sheets from isomorphous replacement when ions of similar size replace cations occupying octahedral holes or sometimes the tetrahedral holes. If this ion has a lower charge than the one it replaces then the lattice will carry an additional negative charge. Deficit charges in smectites are compensated by cations (usually Na, K or Ca) sorbed between the three-layer sandwich. These are held relatively loosely and give rise to exchange properties.

It is believed that the clay characteristics and elemental composition play a role in determining catalytic activity. For example, on slurrying with water, bentonite clays swell which may allow strontium ions to penetrate and exchange between the layers thus improving the distribution of strontium. On drying and firing the clay structure dehydroxylates and collapses and at the higher temperatures new phases are formed. Traces of various elements, can cause substantial changes in the rate of formation and the temperature required for the production of these high temperature phases. Clearly the nature of the clay may have a profound influence on the generation of catalytically active species.

As will be shown later it has also been possible to prepare in the laboratory synthetic analogues of bentonite clays, demonstrating that the elemental composition of the clay is a critical factor, but not necessarily the only factor, in the formation of active and selective components.

The results clearly show the importance of the minor elements, particularly iron (Fe), in the preparation, and it is thought that these elements may play a role in promoting the formation of the high temperature phases during calcination, that are catalyticaly active, rather than having a direct role in the performance of the catalyst. By manipulation of the elemental composition of the synthetic analogues it was possible to gain some understanding of the preferred composition although it was not practical to optimise all constituents due to the complexity of the mixture. The data indicated the following preferred atom ratios for the major constituents quoted relative to silicon (Si)

| Element | Atom Ratio to Si |
|---|---|
| Sr | 3:1 |
| Al | 3:1-1:1 |
| Mg | 0.1:1 |
| Fe | 0.1:1 |
| Na | 0.1:1 |

Although these experiments have identified preferred compositions the mode of preparation and structural arrangement may also be important. For example synthetic clay based catalysts were usually prepared by mixing ingredients in solution, followed by dispersion of solid $SiCO_3$ to form a slurry, drying and calcination. However preparation and drying of the synthetic clay followed by dry grinding with $SiCO_3$ and then calcination produced a catalyst with an inferior performance. This result suggests that the degree of dispersion of the elemental constituents and/or structural development may also contribute to catalytic activity.

BRIEF DESCRIPTION OF THE DRAWINGS

The invention is hereinafter exemplified with reference to the accompanying drawing labelled FIG. 1 which shows a flow diagram for a process involving, inter alia, the oxidative coupling of methane.

BEST METHOD OF CARRYING OUT THE INVENTION

Figure 1:
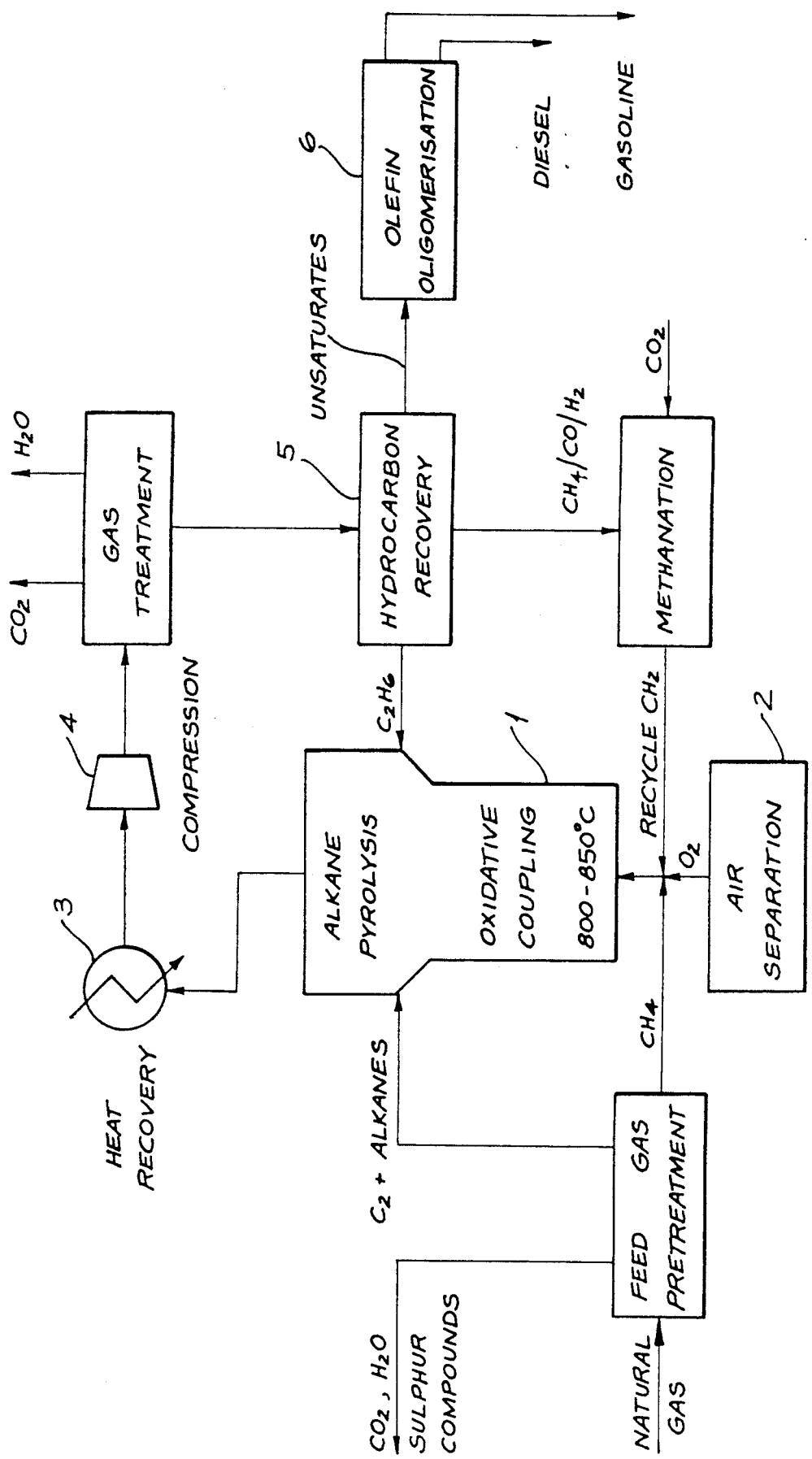

An example of the use of a catalyst which comprises the present invention will now be described by reference to FIG. 1.

Raw natural gas from which most of the C5+ hydrocarbons have been removed, is treated to remove carbon dioxide, water and sulphur compounds and separated into two streams, one comprising substantially methane and the other ethane, propane and higher alkanes. The methane is injected into a fluidised bed reactor 1 along with oxygen extracted by an air separation unit 2. The fluidised bed 1 contains a catalyst according to the present invention. The temperature of the fluidised bed is maintained in the range from 800° to 850° C. Ethane, propane and higher alkanes are injected into the top of the fluidised bed where they are pyrolysed. Gas taken from the top of the fluidised bed is passed through a heat exchanger 3 and then through a compressor 4.

Carbon dioxide and water are removed from the product gas which is then subjected to cryogenic hydrocarbon recovery in a cryogenic unit 5. Ethane recovered from the cryogenic unit is injected back into the top of the fluidised bed reactor. Olefins recovered from the cryogenic unit may be oligomerised in an oligomerisation unit 6 to provide specification grade diesel and/or gasoline. Methane, carbon monoxide and hydrogen recovered from the cryogenic unit 5 may be combined with carbon dioxide to provide methane which is recycled to the bottom of the fluidised bed reactor.

Embodiments of catalysts according to the present invention are described in the following examples.

Catalyst performance was tested in both ceramic (4-6 mm ID) tubular fixed bed reactors and a quartz (30 mm ID) fluidised bed reactor, at atmospheric pressure. Reactant gas consisted of a mixture of $CH_4$ and $O_2$ alone, no diluent was used. In the case of the fixed bed reactors, in order to avoid excessive exotherms across the catalyst bed, either the $O_2$ content of the feed gas was kept low or very low gas flow rates were used when the feed gas contained high (20%) $O_2$ levels. The fluidised-bed reactor operated isothermally under all conditions due to its excellent heat transfer characteristics.

Reactors were raised to temperature usually under a flow of $N_2$ and then switched to the desired reactant flow at the start of a run. The performance of the catalyst was normally determined over a range of flow rates, temperatures and gas compositions, however for comparative purposes in the examples given below data have been selected for constant operating conditions. Where necessary these have been obtained by graphical interpolation in order to eliminate differences in temperature and flow rate from run to run. The reported results include methane conversion $C_2$+hydrocarbon selectively and $C_2$+hydrocarbon yield calculated on a carbon mole basis.

EXAMPLES 1 TO 7

These examples illustrate the improved performance of catalysts containing bentonite clay. $SrCO_3$, $SrCO_3$ containing bentonite and kaolinite clays and sodium (Na) promoted catalysts were prepared by intimately mixing the dry components and then slurrying in water. The slurry was heated until a thick paste was formed and then dried overnight at 150° C. The resultant dried cake was crushed, sized to $-1.2+0.6$ mm, before firing in air at 850° C. for 2.5 hours. A sample of the $SrCO_3$ catalyst was also fired in air at 950° C. The performance of these catalysts at 750° C. in a 6 mm ID reactor using a feed gas containing 95% $CH_4$, 5% $O_2$ and a pseudo-contact time (W/F—weight of catalyst divided by flow rate at operating pressure and temperature (OPT) of 0.02 gs ml$^{-1}$ (OPT) is summarised in Table I.

Figure 2:
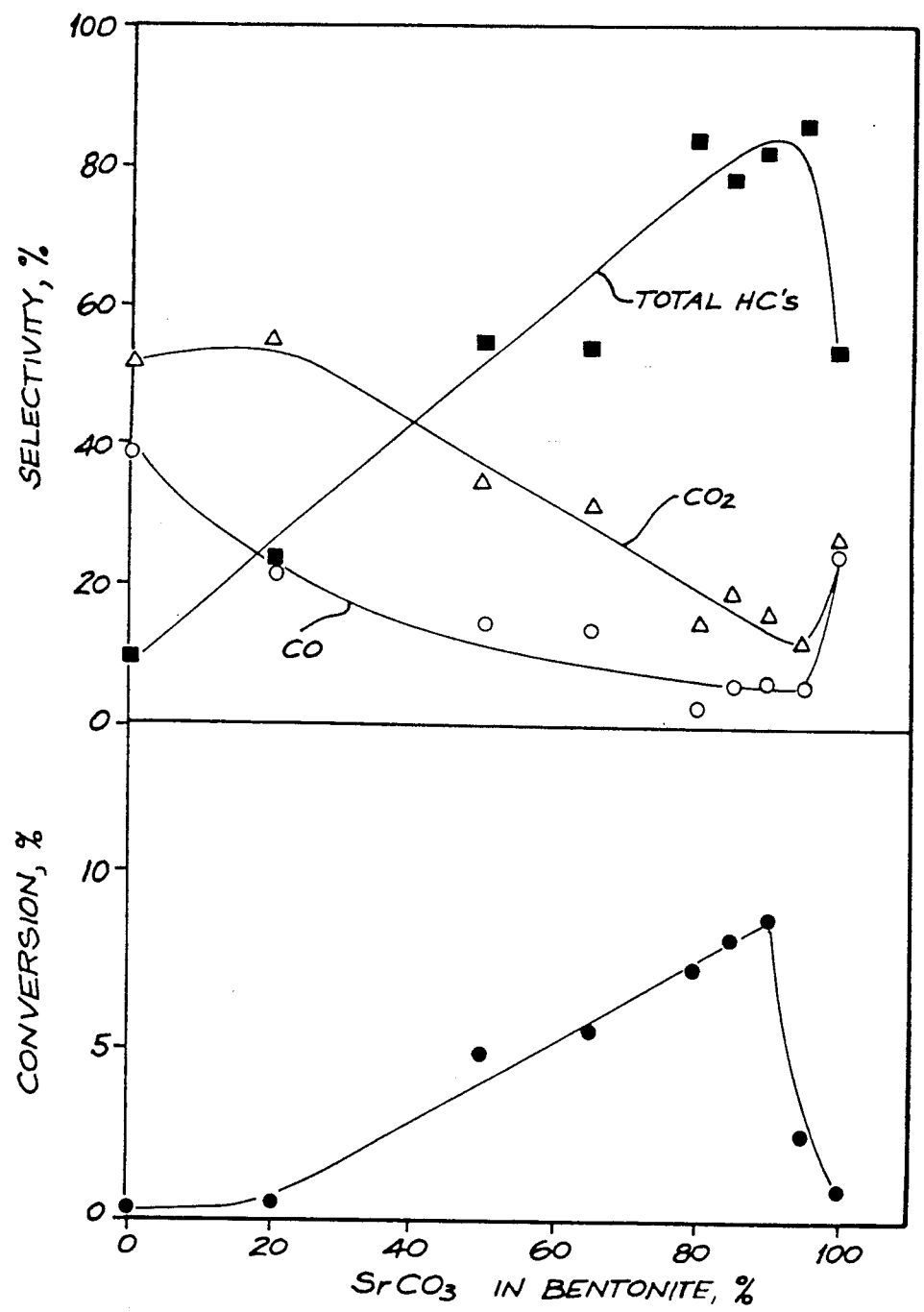
FIG. 2 is a graph showing the variation of the methane conversion and hydrocarbon selectivity with the strontium carbonate content of a catalyst according to the present invention.

The addition of bentonite clay was optimised by investigating the variation in performance as a function of % bentonite added. FIG. 2 shows the relatively poor performance of the strontium carbonate and the bentonite alone and the optimum performance for mixtures containing 80 to 90% w/w strontium carbonate (also compare example 4 with example 1 and 2 in Table I) although mixtures containing from 40% to 95%, and preferably 60% to 90% w/w showed noticeable improvement over strontium carbonate. As a consequence all further studies were conducted using 20% w/w of clay additive. A similar study of the influence of kaolinite addition showed that these catalysts have an inferior performance (example 6). Table IV also shows that after use at 850° C. a somewhat improved performance was obtained on returning to 750° C. (example 6) although still inferior to that of bentonite catalysts (example 4). Thus although kaolinite addition initially resulted in a poorer performance than $SrCO_3$ alone it is evident that the subsequent usage resulted in a significantly improved catalyst. Thus pretreatment conditions play an important role in establishing catalytic activity.

Promotion of these catalysts by Group IA elements was also demonstrated. Table I shows that addition of 2% w/w sodium carbonate ($Na_2CO_3$) to give a Na:Sr atom ratio of 1:49 enhanced performance of both $SrCO_3$ (example 3) and the bentonite catalyst (example 5) by improving hydrocarbon selectivity. There was some evidence of Na promotion of the kaolinite catalyst (example 7) although performance was still poor.

TABLE I

| | Influence of bentonite and kaolinite addition and Na promotion | | | |
|---|---|---|---|---|
| Example No. | Catalyst Components | $CH_4$ conversion (%) | Hydrocarbon Selectivity (%) | Hydrocarbon Yield (%) |
| 1 | $SrCO_3$(850° C.) | 0.5 | 47 | 0.2 |
| 2 | $SrCO_3$(950° C.) | 0.6 | 52 | 0.3 |
| 3 | Na/$SrCO_3$ | 0.8 | 80 | 0.6 |
| 4 | $SrCO_3$/bentonite | 7.0 | 83 | 5.8 |
| 5 | Na/$SrCO_3$/bentonite | 6.6 | 90 | 5.9 |
| 6 | $SrCO_3$/kaolinite | 1.7 | 18 | 0.3 |
| | After use at 850° C. | 5.0 | 64 | 3.1 |
| 7 | Na/$SrCO_3$/kaolinite | 2.7 | 40 | 1.0 |
| | After use at 850° C. | 4.7 | 65 | 3.0 |

EXAMPLES 8-11

These examples demonstrate the influence of other Group IA additives on the performance of $SrCO_3$/20% bentonite catalyst. Catalysts were prepared as described above with the carbonates of Li, K, Rb and Cs being added so that the atom ratio of alkali metal to strontium was maintained at 1:49. Table II shows the performance of these catalysts under the same conditions as Table I namely temperature 750° C., reactant gas 95% $CH_4$, 5% $O_2$ and W/F=0.02 gs ml$^{-1}$ (OPT). For comparison example 5 from Table I is given. Clearly Li and K addition results in promotion and a hydrocarbon selectivity similar to that for Na. Activity as shown by $CH_4$ conversion is reduced. Rb and Cs addition results in an inferior performance (compare examples 10 and 11 with example 5, Table I).

TABLE II

Influence on Group IA promoters on $SrCO_3$/bentonite catalysts

| Example No. | Catalyst Additive | $CH_4$ conversion (%) | Hydrocarbon Selectivity (%) | Hydrocarbon Yield (%) |
|---|---|---|---|---|
| 5 | Na | 6.6 | 90 | 5.9 |
| 8 | Li | 5.0 | 87 | 4.1 |
| 9 | K | 5.1 | 89 | 4.4 |
| 10 | Rb | 4.9 | 70 | 3.4 |
| 11 | Cs | 4.1 | 66 | 2.6 |

EXAMPLES 12-19

The following examples demonstrate the variation in catalyst performance with clay type.

Catalysts were prepared by grinding together $SrCO_3$ and 20% w/w clay with water to give a slurry which was dried at 110° C. All catalysts were calcined in air at 850° C. for 2 hours. Performance was measured in a 4 mm ID reactor at 800° C. using a reactant gas of 80% $CH_4$ and 20% $O_2$, and a pseudo contact time of 0.12 gs ml$^{-1}$ (OPT).

Table III shows the results for a variety of clay additives and includes for comparison the bentonite catalyst the subject of example 4. The superiority of the bentonite clay to the other clays in both $CH_4$ conversion and hydrocarbon selectivity is demonstrated. It is also evident that the addition of most clays gives a better hydrocarbon selectivity than $SrCO_3$ alone.

TABLE III

Influence of clay type

| Example No. | Catalyst Clay Additive | $CH_4$ conversion (%) | Hydrocarbon Selectivity (%) | Hydrocarbon Yield (%) |
|---|---|---|---|---|
| 12 | Kaolinite | 19.7 | 31 | 6.0 |
| 13 | Saponite | 22.4 | 33 | 7.4 |
| 14 | Glauconite | 21.5 | 38 | 8.2 |
| 15 | Attapulgite | 19.5 | 21 | 4.1 |
| 16 | Chlorite | 20.0 | 34 | 6.8 |
| 17 | Nontronite | 21.0 | 42 | 8.8 |
| 18 | Bentonite (as in Example 4) | 25.1 | 53 | 13.3 |
| 19 | $SrCO_3$ alone | 24.2 | 29 | 7.0 |

EXAMPLES 20-23

The improved performance of bentonite containing catalysts in a fluidised-bed reactor is demonstrated in these examples.

Catalysts were prepared in a manner similar to that described for examples 1 to 7 although in larger batches. After drying, the cake was ground, pressed into discs and then crushed and sieved to give particles of size −250+150 um. The sized catalysts were then calcined and hardened by firing in $CO_2$ at 1000° C. for 4 hours as described in a co-pending patent application entitled "Hardening of catalyst particles".

Catalyst performance was measured in a 30 mm ID fluidised-bed reactor using bed depths of around 30 mm. Reactant gas flows were in the range 1-2 l/min (STP). Table IV illustrates the improved performance with bentonite addition and promotion by Na.

TABLE IV

Catalyst performance in a fluidised-bed reactor

| | Catalyst | | | |
|---|---|---|---|---|
| | $SrCO_3$ | $SrCO_3$ 20% w/w bentonite | $SrCO_3$ 20% w/w bentonite 2 atom % Na | |
| | Example No. | | | |
| | 20 | 21 | 22 | 23 |
| Feed gas | | | | |
| Oxygen (% v/v) | 5.0 | 4.7 | 11.6 | 1.4 |
| Methane (% v/v) | 95.0 | 95.3 | 88.4 | 88.6 |
| Temperature (°C.) | 805 | 793 | 854 | 849 |
| Methane conversion (%) | 5.2 | 9.3 | 16.4 | 17.7 |
| Oxygen consumption (%) | 70.5 | 100.0 | 100.0 | 99.0 |
| Selectivity to hydrocarbons (%) | 62.0 | 84.2 | 71.0 | 77.0 |
| Hydrocarbon yield (% input methane) | 3.2 | 7.8 | 11.6 | 13.6 |

EXAMPLE 24

Processes for the preparation of catalysts according to the present invention are described below in this example.

Samples of a $SrCO_3$/bentonite catalyst were heated at 1000° C. for 4 hours in (a) an inert gas, nitrogen ($N_2$) and (b) carbon dioxide ($CO_2$) atmospheres. The hardening process was accompanied by considerable shrinkage in the size of the individual particles and this resulted in a reduction in their surface areas. Surface area measurements were made by the conventional BET techniques on the fresh untreated catalyst and those heated in $N_2$ and $CO_2$ atmospheres. The results are given in the accompanying Table V.

TABLE V

| Sample | Surface Area m$^2$/g |
|---|---|
| Fresh untreated | 15.0 |
| Heated in $N_2$ (4 hours 1000° C.) | 7.1 |
| Heated in $CO_2$ (4 hours 1000° C.) | 0.3 |

Catalysts hardened in an atmosphere of $CO_2$ have been successfully used in fluidised-bed reactors for many hours with no measurable weight loss due to attrition and dust formation.

EXAMPLES 25-44

Bentonite has been shown to provide the best catalytic performance and it is of relevance to compare it with a catalyst produced from $SrCO_3$ and kaolinite clay. The performance of the latter catalyst was inferior even to $SrCO_3$ (see examples 6 & 7) although performance improved after use to the extent that it was better than $SrCO_3$ but still very inferior to bentonite catalysts.

A comparison of the elemental composition of these two clays is given in the Table VI below.

TABLE VI

| | Chemical Analysis of Clays (% w/w) | |
|---|---|---|
| | Bentonite | Kaolinite |
| Al | 8.8 | 10.2 |
| Si | 24.3 | 21.6 |
| Ca | 1.5 | <0.04 |
| Fe | 3.1 | 0.1 |
| Na | 1.7 | 0.09 |
| K | 0.33 | 0.38 |
| Mg | 1.4 | 0.07 |
| Mn | <0.1 | 0.1 |
| Ti | 0.14 | <0.04 |
| S | 0.4 | <0.1 |

A feature is the relatively low level of Ca, Fe, Na and Mg in kaolinite due to its low cationic exchange capacity. It is thought that this low cation content may contribute to the poorer catalytic performance of kaolinite although it should be recognised that it also has a different structure (1:1 compared with 2:1 for bentonite). Studies with bentonite clays from different sources, produced good catalysts although performance was variable and again it is thought the varying cation contents may have contributed.

From the above it is clear that the mode of catalytic activation by clays is complex and as yet not understood. In view of the enormous variability in clays both in structure and elemental composition it was considered relevant to attempt to synthesize a catalyst using the elemental composition of an appropriate clay. If successful this would eliminate uncertainties due to variations in the compositions of natural clays and possibly provide further information on the mode of clay activation.

The study was commenced using the bentonite elemental composition together with $SrCO_3$. Appropriate compounds of all the component elements were selected and combined in the required proportions. After drying and firing the catalytic performance was found to be very similar to that achieved with a natural bentonite clay additive. Thus the synthetic mixture of clay components with $SrCO_3$ also produces the desired destabilisation of the carbonate phase and the development of the catalytic active oxide structure. This result does suggest that the nature of the clay structure is not as important as the elemental constituents.

In view of the success of this study it was now possible to investigate the influence of variations in the composition of the synthetic clay and results are given in examples 25-44.

The data show the importance of maintaining the minor elements, particularly Fe, in the preparation in order to achieve the most active catalyst. It is suggested these elements, although not necessarily crucial to the catalytic performance may have a role in promoting the formation of the desired high temperature phases during calcination. In view of the number of elemental constituents it has not been possible to optimise their concentrations however some indication of the preferred levels was obtained. Group IIa elements such as Sr are essential and should be in an atomic ratio to Si of about 3:1. The Al:Si can vary widely however the preferred atomic ratio lies between 3:1 and 1:1. The presence of Mg and/or Ca in the Sr based catalyst is not essential, however, higher reaction rates are obtained when added at levels giving an atomic ratio with Si or about 0.1:1. As noted above Fe is considered essential with a preferred atomic ratio with Si of about 0.1:1, whereas trace amounts of Mn and Ti (atomic ratios with Si of 0.02:1) do not appear essential. The presence of Group IA elements, particularly Na or K is important preferably with a Na:Si atomic ratio of at least 0.1:1.

The above provide preferred levels of elemental constituents, however it is believed that the mode of preparations and possibly some structural arrangement may also be important. Synthetic clays were usually prepared by forming a gel-like product by adding colloidal silica to homogeneous solutions of all other ingredients apart from $SrCO_3$. $SrCO_3$ powder was then added slowly to the gel to form a paste which was dried and finally calcined. In other experiments the synthetic clay was produced and dried without adding $SrCO_3$. Combination of the dried and crushed clay with $SrCO_3$ was achieved by dry grinding. After calcination the catalyst was found to have an inferior performance. This result indicates that dispersion of the catalyst constituents and/or structural development also contribute to catalytic activity.

The following examples demonstrate the preparation and performance of catalysts prepared using a synthetic clay formulation and the variation of performance with elemental composition.

The preparation usually involves the formation of a gel type of product by adding colloidal silica to a warm, homogeneous solution of all ingredients other than $SrCO_3$. The solid $SrCO_3$ was added slowly to the gel with heating and stirring which was continued even after the completion of $SrCO_3$ addition in order that all undissolved solid may be uniformly dispersed. The final pasty mass was dried in air or under vacuum at 120° C. The oven-dried material was calcined at 1000° C. in a stream of pure $CO_2$ for 4 h before catalytic activity testing. The calcined product was pressed under 10-15 tonnes/cm$^2$ and then crushed and sieved to 0.6-1.2 mm particles.

Catalyst performance was determined in a 4 mm ID reactor at 800° C. using a reactant gas composition of 95% $CH_4$, 5% $O_2$ and W/F=0.02 gsml$^{-1}$ (OPT).

Table VII gives the nominal elemental composition (as an atomic ratio with silicon set to 100) of bentonite clay and the composition and performance of a Na promoted, $SrCO_3$ and natural bentonite catalyst (example 25), a synthetic clay catalyst of similar composition (example 26) and further synthetic clay catalysts with a range of compositions (examples 27-44).

The results demonstrate that catalysts synthesized with the same elemental constituents as the bentonite have a performance at least as good as the natural clay. Further there is evidence that some improvement can be achieved by optimisation of the composition.

TABLE VII

| Composition and performance of synthetic clay catalysts (atom ratio) | | | | | | | | | | | | |
|---|---|---|---|---|---|---|---|---|---|---|---|---|
| | | CATALYST NO. | | | | | | | | | | |
| Element | Bentonite | 25 | 26 | 27 | 28 | 29 | 30 | 31 | 32 | 33 | 34 | 35 |
| Sr | | 313 | 313 | 313 | 313 | 313 | 313 | 313 | 313 | 313 | 313 | 313 |
| Si | 100 | 100 | 100 | 100 | 100 | 100 | 100 | 100 | — | 100 | 100 | 100 |
| Al | 37.9 | 37.9 | 38 | 38 | 38 | 38 | 38 | — | 219 | 38 | 38 | 38 |

TABLE VII-continued

Composition and performance of synthetic clay catalysts (atom ratio)

| Element | | | | | | | | | | | | |
|---|---|---|---|---|---|---|---|---|---|---|---|---|
| Na | 8.4 | 14.6 | 13 | 13 | 13 | 13 | — | — | — | 13 | 13 | 13 |
| Ca | 4.4 | 4.4 | 4 | 4 | 4 | 4 | — | — | — | — | — | 11 |
| Mg | 6.9 | 6.9 | 7 | 7 | 7 | 7 | — | — | — | — | 11 | — |
| K | 0.9 | 0.9 | 0.7 | — | — | — | — | — | — | — | — | — |
| Fe | 6.4 | 6.4 | 6.5 | 6.5 | — | — | — | — | — | 6.5 | 6.5 | 6.5 |
| Ti | 0.3 | 0.3 | 0.3 | — | — | — | — | — | — | — | — | — |
| Mn | 0.2 | 0.2 | 0.2 | — | 2.3 | — | — | — | — | — | — | — |
| S | 1.6 | 1.6 | 13 | 13 | — | — | — | — | — | 13 | 13 | 13 |
| P | 0.3 | 3.4 | — | — | — | — | — | — | — | — | — | — |
| PERFORMANCE DATA | | | | | | | | | | | | |
| $CH_4$ conversion % | | 5.4 | 3.4 | 3.4 | 5.8 | 4.9 | 2.5 | 3.4 | 3.1 | 3.4 | 4.0 | 3.2 |
| Hydrocarbon Selectivity (%) | | 87 | 92 | 91 | 87 | 86 | 65 | 47 | 74 | 92 | 91 | 92 |

| Element | CATALYST NO. | | | | | | | | |
|---|---|---|---|---|---|---|---|---|---|
| | 36 | 37 | 38 | 39 | 40 | 41 | 42 | 43 | 44 |
| Sr | 250 | 200 | 150 | 290 | 290 | 290 | 290 | 290 | 290 |
| Si | 100 | 100 | 100 | 100 | 100 | 100 | 100 | 100 | 100 |
| Al | 38 | 38 | 38 | 38 | 38 | 38 | 60 | 100 | 38 |
| Na | 13 | 13 | 13 | 13 | 13 | 13 | 13 | 13 | — |
| Ca | — | — | — | — | — | — | — | — | 20 |
| Mg | 11 | 11 | 11 | 11 | 11 | 11 | 11 | 11 | 11 |
| K | — | — | — | — | — | — | — | — | — |
| Fe | 6.5 | 6.5 | 6.5 | 64 | 32 | 16 | 16 | 16 | 6.5 |
| Ti | — | — | — | — | — | — | — | — | — |
| Mn | — | — | — | — | — | — | — | — | — |
| S | 13 | 13 | 13 | 128 | 65 | 32 | 32 | 32 | 13 |
| P | — | — | — | — | — | — | — | — | — |
| PERFORMANCE DATA | | | | | | | | | |
| $CH_4$ conversion % | 3.6 | 5.9 | 5.0 | 6.1 | 3.1 | 5.6 | 4.9 | 5.5 | 6.1 |
| Hydrocarbon Selectivity (%) | 90 | 74 | 60 | 65 | 89 | 90 | 90 | 90 | 77 |

We claim:

1. A catalyst for the oxidative coupling of methane, comprising a compound of a Group IIA element that is capable, under reaction conditions, of existing at least partly in its oxide or carbonate forms, intimately mixed with a clay capable of enhancing the catalyst performance.

2. A catalyst as claimed in claim 1, in which the Group IIA element is selected from the group comprising strontium, calcium, barium and magnesium.

3. A catalyst as claimed in claim 2 in which the Group IIA element is strontium.

4. A catalyst as claimed in claim 1 in which the compound of the Group IIA element is capable, under reaction conditions, of existing at least partly in its oxide form.

5. A catalyst as claimed in claim 4 in which the compound of the Group IIA element is strontium carbonate.

6. A catalyst as claimed in any one of claims 1 to 5 in which the catalyst additionally contains a group IA element that is capable, under the reaction conditions of existing at least partly in its oxide or carbonate form.

7. A catalyst as claimed in claim 6 in which the compound of the Group IA element is sodium carbonate.

8. A catalyst as claimed in claim 1, in which the clay is a crystalline clay, a paracrystalline clay or a synthetic analogue thereof.

9. A catalyst as claimed in claim 8 in which the clay contains clay minerals selected from the group comprising kaolins, serpentines, smectites, illites or micas, glauconites and chlorites and vermiculites and synthetic analogues thereof.

10. A catalyst as claimed in claim 9 in which the clay contains clay minerals of the smectite group or a synthetic analogue thereof.

11. A catalyst as claimed in claim 10 in which the clay contains the clay mineral bentonite or a synthetic analogue thereof.

12. A catalyst as claimed in claim 1 in which the Group IIA compound is present in the catalyst an amount of from 40% to 95% of the total weight of the Group IIA compound and the clay in the catalyst.

13. A catalyst as claimed in claim 12 in which the Group IIA compound is present in the catalyst in an amount of from 60 to 90% of the total weight of the Group IIA compound and the clay in the catalyst.

14. A catalyst as claimed in claim 12 in which the Group IIA compound is present in the catalyst in an amount of from 80% to 90% of the total weight of the Group IIA compound and the clay in the catalyst.

15. A catalyst as claimed in claim 1 in which the catalyst has been heated to a temperature of at least 700° C. after the Group IIA compound and the clay have been intimately mixed.

16. A catalyst as claimed in claim 15 in which the catalyst has been heated to a temperature of at least 1000° C.

17. A catalyst as claimed in claim 15 or claim 16 in which the heating was conducted for at least 2 hours.

18. A catalyst as claimed in claim 15 in which the heating was carried out in an atmosphere selected from the gases comprising nitrogen and carbon dioxide.

* * * * *

UNITED STATES PATENT AND TRADEMARK OFFICE
CERTIFICATE OF CORRECTION

PATENT NO. : 5,066,629
DATED : November 19, 1991
INVENTOR(S) : Christopher LUKEY et al It is certified that error appears in the above-indentified patent and that said Letters Patent is hereby corrected as shown below:

Column 3, Line 50, after "believed", insert -- that --.

Column 4, Line 58, change "SiCO$_3$" to -- SrCO$_3$ --.

Column 4, Line 60, change "SiCO$_3$" to -- SrCO$_3$ --.

Column 5, Line 66, after "conversion", insert -- , --.

Column 6, Line 31, change "IV" to -- I --.

Column 7, Line 12, after "example 5", delete -- , Table I --.

UNITED STATES PATENT AND TRADEMARK OFFICE
CERTIFICATE OF CORRECTION

PATENT NO. : 5,066,629    Page 2 of 3
DATED : November 19, 1991
INVENTOR(S) : Christopher LUKEY et al It is certified that error appears in the above-indentified patent and that said Letters Patent is hereby corrected as shown below:

Column 8, Line 8, Table IV, align:

to appear:

| TABLE IV | | | | | TABLE IV | | | | |
|---|---|---|---|---|---|---|---|---|---|
| Catalyst performance in a fluidised-bed reactor | | | | | Catalyst performance in a fluidised-bed reactor | | | | |
| | Catalyst | | | | | Catalyst | | | |
| | SrCO₃ | SrCO₃ 20% w/w bentonite | SrCO₃ 20% w/w bentonite 2 atom % Na | | | SrCO₃ | SrCO₃ 20% w/w bentonite | SrCO₃ 20% w/w bentonite 2 atom % Na | |
| | Example No. | | | | | Example No. | | | |
| | 20 | 21 | 22 | 23 | | 20 | 21 | 22 | 23 |
| Feed gas | | | | | Feed gas | | | | |
| Oxygen (% v/v) | 5.0 | 4.7 | 11.6 | 1.4 | Oxygen (% v/v) | 5.0 | 4.7 | 11.6 | 1.4 |
| Methane (% v/v) | 95.0 | 95.3 | 88.4 | 88.6 | Methane (% v/v) | 95.0 | 95.3 | 88.4 | 88.6 |
| Temperature (°C) | 805 | 793 | 854 | 849 | Temperature (°C) | 805 | 793 | 854 | 849 |
| Methane conversion (%) | 5.2 | 9.3 | 16.4 | 17.7 | Methane conversion (%) | 5.2 | 9.3 | 16.4 | 17.7 |
| Oxygen consumption (%) | 70.5 | 100.0 | 100.0 | 99.0 | Oxygen consumption (%) | 70.5 | 100.0 | 100.0 | 99.0 |
| Selectivity to hydrocarbons (%) | 62.0 | 84.2 | 71.0 | 77.0 | Selectivity to hydrocarbons (%) | 62.0 | 84.2 | 71.0 | 77.0 |
| Hydrocarbon yield (% input methane) | 3.2 | 7.8 | 11.6 | 13.6 | Hydrocarbon yield (% input methane) | 3.2 | 7.8 | 11.6 | 13.6 |

Column 8, Line 19, in Table IV, change "1.4" to -- 11.4 --.

Column 9, Line 43, change "catalytic" to -- catalytically --.

Column 9, Line 52, after "suggested", insert -- that --.

Column 10, Line 5, change "or" to -- of --.

UNITED STATES PATENT AND TRADEMARK OFFICE
CERTIFICATE OF CORRECTION

PATENT NO. : 5,066,629
DATED : November 19, 1991
INVENTOR(S) : Christopher Lukey, et al It is certified that error appears in the above-indentified patent and that said Letters Patent is hereby corrected as shown below:

Column 12, claim 12, line 42, after "catalyst", insert --in--.

Signed and Sealed this

Eighteenth Day of October, 1994

Attest:

BRUCE LEHMAN

Attesting Officer     *Commissioner of Patents and Trademarks*